US006013510A

United States Patent [19]

Harris et al.

[11] Patent Number: 6,013,510

[45] Date of Patent: Jan. 11, 2000

[54] **IDENTIFICATION OF A DNA REGION POTENTIALLY USEFUL FOR THE DETECTION OF *MYCOBACTERIUM KANSASII***

[75] Inventors: James M. Harris, Columbia; Qimin You, Lutherville, both of Md.

[73] Assignee: Becton, Dickinson and Company, Franklin Lakes, N.J.

[21] Appl. No.: 08/937,580

[22] Filed: Sep. 25, 1997

[51] Int. Cl.[7] .............................. C12N 1/12; C12Q 1/68; C07H 21/04

[52] U.S. Cl. .......................... 435/253.1; 435/6; 435/69.1; 435/91.1; 536/24.3; 536/24.32

[58] Field of Search ............................. 435/6, 69.1, 91.1, 435/253.1; 536/24.3, 24.32

[56] References Cited

FOREIGN PATENT DOCUMENTS

| | | |
|---|---|---|
| 0 707 075 | 4/1996 | European Pat. Off. . |
| WO 96 00783 | 1/1996 | WIPO . |

OTHER PUBLICATIONS

T. Rogall, et al. "Differentiation of Mycobacterium species by direct sequencing of amplified DNA" *J. Gen. Microbiol.* 136:1915–1920 (1990).

B. Boddinghaus, et al. "Detection and Identification of Mycobacteria by Amplification of rRNA" *J. Clin. Microbiol.* 28:1751–1759 (1990).

M. Yang, et al. "Isolation of a DNA Probe for Identification of *Mycobacterium kansasii*, Including the Genetic Subgroup" *J. Clin. Microbiol.* 31:2769–2772 (1993).

E. Tortoli, et al. "Evaluation of a Commercial DNA Probe Assay for the Identification of *Mycobacterium kansasii*" *J. Clin. Microbiol. Infe. Dis.* 13:264–267 (1994).

B. C. Ross, et al. "Identification of a Genetically Distinct Subspecies of *Mycobacterium kansasii*" *J. Clin. Microbiol.* 30:2930–2933 (1992).

Z. H. Huang, et al. "Identification of *Mycobacterium kansasii* by DNA Hybridization" *J. Clin. Microbiol.* 29:2125–2129 (1991).

Philipp et al, "An integrated map of the genome of the tubercule bacillus, *Mycobacterium tuberculosis* H37Rv, and comparison with *Mycobacterium leprae*", Proc. Natl. Acad. Sci., USA. vol. 93, pp. 3132–3137, Apr. 1, 1996.

EMBL55 database, Accession No. Z94121, MPSRCH, n.a. database search, Apr. 15, 1997

*Primary Examiner*—James C. Housel
*Assistant Examiner*—Rodney P. Swartz
*Attorney, Agent, or Firm*—Donna R. Fugit

[57] ABSTRACT

Disclosed herein is a newly-identified DNA sequence from *Mycobacterium kansasii* designated KATS2. Also disclosed are methods, oligonucleotide probes, amplification primers, and kits for the detection of *M. kansasii* nucleic acids. *M. kansasii*-specific methods, probes, amplification primers, and kits are preferred.

10 Claims, 10 Drawing Sheets

FIG-1

Typical *M. kansasii* KATS2 sequence:

GTTGG CGTGG AGCTG TCTGA GCGAG GTCAG GTCAT GGTCG CCACA GGCGA TGCGG CCCAG
Primer E1C →
CCATG CGTCG GCCAT CGACG GGTCG GCGTC GGTGG CGGCG ACGAA *CTCGG G*TAAC GCGGC CGCTG GTCCC TGGCT GCTCT TGACC GCCAT AGCTC GATCG AAATG CCTAC GGGCA GTGAG
Primer I4 and I5 ←→
CAAAT CACCC ATCGT ATCCA CCATC CTCGA CAGCG TGGTG GTATT CGTCC CGAAA GTGGG ACGTC CGCCT CATGA CGTTG TGCCG CAACG TTGAT CGAGT CACTG TGTAG CAATC GACAT
Primer I2 ←
GGTGA CGGGT TCGAG GCTGA CGTAA CGGTT CTCGG CGCGG AACAT CTCCA TCTCC ACCAG C
Primer E3 ←

FIG-2

Atypical *M. kansasii* KATS2 sequence:

GTTGG CGTGG AGCTG TCTGA GCGAG GTCAG GTCAT GGTCG CCACA GGCGA TGCGG CCCAG
Primer E1C→
CCATG CGTCA GCCAT CGACG GGTCG GCGTC GGTGG CGGCG ACGAA *CTCGG G*TAAC GCGGG TTCTG GTCCC TGGCT GCTCT TGATC GCCAT CGCTC GATCG AAATG CCTAC GGGCA GTGAG
Primer I4 and I5 ←→
CAAAT CAGCC ATTGT ATCCA CCATC CTGGA CAGCG TGGCG GTAAT CGTTC CGCAA CGGGG AAGTC TGCCT CATCA CGTTG TGGCG CAACG TTGAT CGAGT CACTT CGTAG CAATC GACAT
Primer I2 ←
GGTGA CCGGC TCGAG ACTGA CGTAA CGATT TTCGG CGCGG AACAT CTCCA TCTCC ACCAG C
Primer E3 ←

FIG-3A KATS2 Alignment

```
Consensus    TCAGGTCATG GTCGCCACAG GCGATGCGGC CCAGCCATGC GTCRGCCATC   50

MKAN-711     .......... .......... .......... .......... ...G......   50
MKAN-714     .......... .......... .......... .......... ...G......   50
MKAN-1201    .......... .......... .......... .......... ...G......   50
MKAN-725     .......... .......... .......... .......... ...G......   50
MKAN-18494   .......... .......... .......... .......... ...G......   50
MKAN-724     .......... .......... .......... .......... ...G......   50
MKAN-11792   .......... .......... .......... .......... ...A......   50
MKAN-1492    .......... .......... .......... .......... ...A......   50
MKAN-8246    .......... .......... .......... .......... ...A......   50

Consensus    GACGGGTCGG CGTCGGTGGC GGCGACGAAC TCGGGTAACG CGGSYKCTGG  100

MKAN-711     .......... .......... .......... .......... ...CCG....  100
MKAN-714     .......... .......... .......... .......... ...CCG....  100
MKAN-1201    .......... .......... .......... .......... ...CCG....  100
MKAN-725     .......... .......... .......... .......... ...CCG....  100
MKAN-18494   .......... .......... .......... .......... ...CCG....  100
MKAN-724     .......... .......... .......... .......... ...CCG....  100
MKAN-11792   .......... .......... .......... .......... ...GTT....  100
MKAN-1492    .......... .......... .......... .......... ...GTT....  100
MKAN-8246    .......... .......... .......... .......... ...GTT....  100
```

FIG-3B KATS2 Alignment

```
Consensus    TCCCTGGCTG CTCTTGAYCG CCATMGCTCG ATCGAAATGC CTACGGGCAG  150

MKAN-711     .......... .......C.. ....A..... .......... ..........  150
MKAN-714     .......... .......C.. ....A..... .......... ..........  150
MKAN-1201    .......... .......C.. ....A..... .......... ..........  150
MKAN-725     .......... .......C.. ....A..... .......... ..........  150
MKAN-18494   .......... .......C.. ....A..... .......... ..........  150
MKAN-724     .......... .......C.. ....A..... .......... ..........  150
MKAN-11792   .......... .......I.. ....C..... .......... ..........  150
MKAN-1492    .......... .......I.. ....C..... .......... ..........  150
MKAN-8246    .......... .......I.. ....C..... .......... ..........  150

Consensus    TGAGCAAATC ASCCATYGTA TCCACCATCC TSGACAGCGT GGYGGTAWTC  200

MKAN-711     .......... .C....C... .......... .C........ ..I....I..  200
MKAN-714     .......... .C....C... .......... .C........ ..I....I..  200
MKAN-1201    .......... .C....C... .......... .C........ ..I....I..  200
MKAN-725     .......... .C....C... .......... .C........ ..I....I..  200
MKAN-18494   .......... .C....C... .......... .C........ ..I....I..  200
MKAN-724     .......... .C....C... .......... .C........ ..I....I..  200
MKAN-11792   .......... .G....I... .......... .G........ ..C....A..  200
MKAN-1492    .......... .G....I... .......... .G........ ..C....A..  200
MKAN-8246    .......... .G....I... .......... .G........ ..C....A..  200
```

FIG-3C

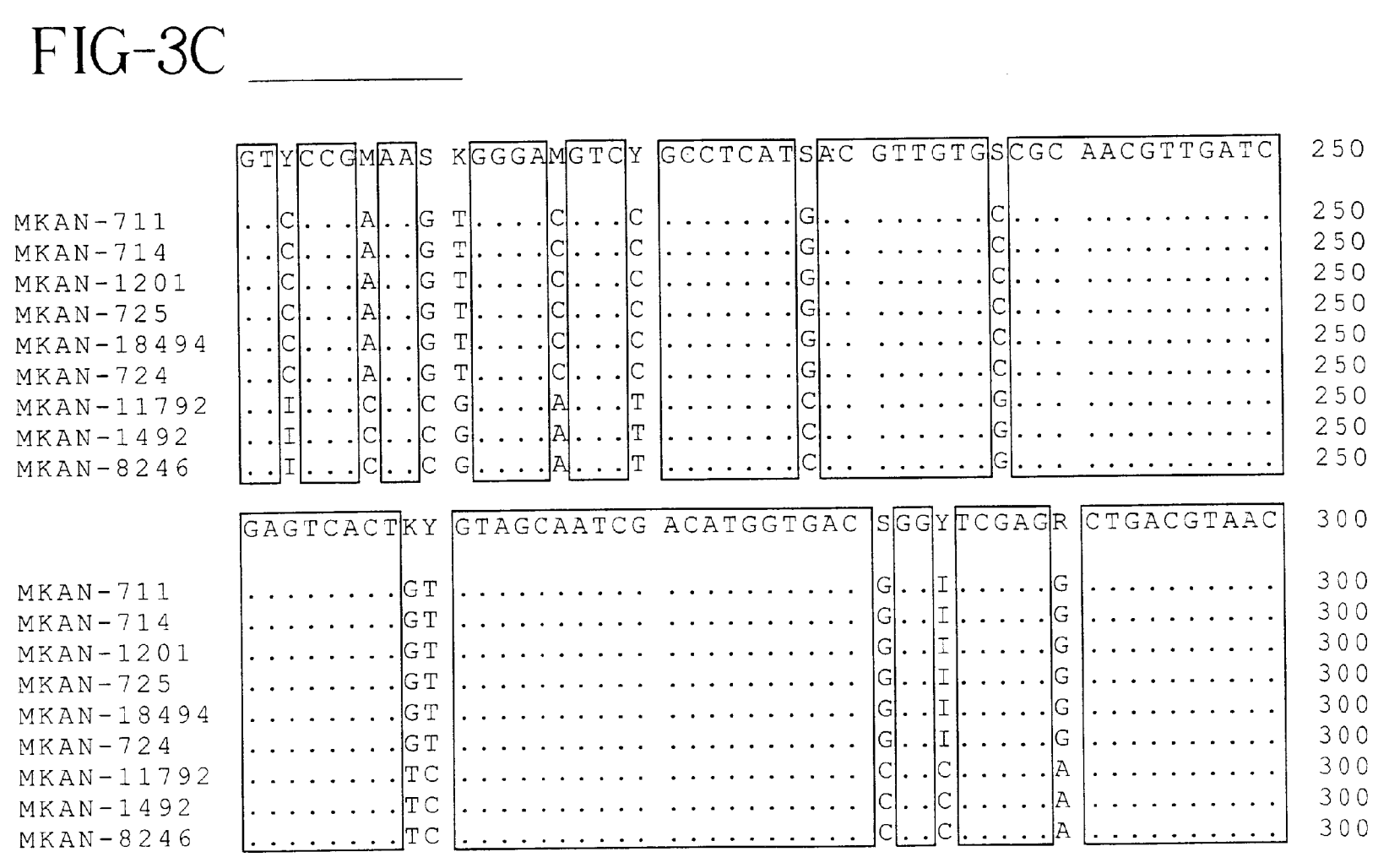

```
           GTYCCGMAAS KGGGAMGTCY GCCTCATSAC GTTGTGSCGC AACGTTGATC 250
MKAN-711   ..C...A..G T....C...C .......G.. ......C... .......... 250
MKAN-714   ..C...A..G T....C...C .......G.. ......C... .......... 250
MKAN-1201  ..C...A..G T....C...C .......G.. ......C... .......... 250
MKAN-725   ..C...A..G T....C...C .......G.. ......C... .......... 250
MKAN-18494 ..C...A..G T....C...C .......G.. ......C... .......... 250
MKAN-724   ..C...A..G T....C...C .......G.. ......C... .......... 250
MKAN-11792 ..T...C..C G....A...T .......C.. ......G... .......... 250
MKAN-1492  ..T...C..C G....A...T .......C.. ......G... .......... 250
MKAN-8246  ..T...C..C G....A...T .......C.. ......G... .......... 250

           GAGTCACTKY GTAGCAATCG ACATGGTGAC SGGYTCGAGR CTGACGTAAC 300
MKAN-711   ........GT .......... .......... G..T.....G .......... 300
MKAN-714   ........GT .......... .......... G..T.....G .......... 300
MKAN-1201  ........GT .......... .......... G..T.....G .......... 300
MKAN-725   ........GT .......... .......... G..T.....G .......... 300
MKAN-18494 ........GT .......... .......... G..T.....G .......... 300
MKAN-724   ........GT .......... .......... G..T.....G .......... 300
MKAN-11792 ........TC .......... .......... C..C.....A .......... 300
MKAN-1492  ........TC .......... .......... C..C.....A .......... 300
MKAN-8246  ........TC .......... .......... C..C.....A .......... 300
```

FIG-3D KATS2 Alignment

| | | |
|---|---|---|
| Consensus | GRTTYTCGG | 309 |
| MKAN-711 | .G..C.... | 309 |
| MKAN-714 | .G..C.... | 309 |
| MKAN-1201 | .G..C.... | 309 |
| MKAN-725 | .G..C.... | 309 |
| MKAN-18494 | .G..C.... | 309 |
| MKAN-724 | .G..C.... | 309 |
| MKAN-11792 | .A..I.... | 309 |
| MKAN-1492 | .A..I.... | 309 |
| MKAN-8246 | .A..I.... | 309 |

FIG-4A

```
             TCAGGTTCRT GGTTCGCCAC AGGCGATGCG GCCCAGCCAT GCGTCRGCCA   50

MGASTRI      ........G. .......... .......... .......... .....A....   50
MKAN-8246    ......-.A. ..-....... .......... .......... .....A....   48
MKAN-1492    ......-.A. ..-....... .......... .......... .....A....   48
MKAN-11792   ......-.A. ..-....... .......... .......... .....A....   48
MKAN-1201    ......-.A. ..-....... .......... .......... .....G....   48
MKAN-714     ......-.A. ..-....... .......... .......... .....G....   48
MKAN-724     ......-.A. ..-....... .......... .......... .....G....   48
MKAN-18494   ......-.A. ..-....... .......... .......... .....G....   48
MKAN-711     ......-.A. ..-....... .......... .......... .....G....   48
MKAN-725     ......-.A. ..-....... .......... .......... .....G....   48

             TCGACGGGTC GGCGTCGGTG GCGGCGACGA ACTCGGGTAA CGCGKSYKCT  100

MGASTRI      .......... .......... .......... .......... ....TCCG..  100
MKAN-8246    .......... .......... .......... .......... ....GGTT..   98
MKAN-1492    .......... .......... .......... .......... ....GGTT..   98
MKAN-11792   .......... .......... .......... .......... ....GGTT..   98
MKAN-1201    .......... .......... .......... .......... ....GCCG..   98
MKAN-714     .......... .......... .......... .......... ....GCCG..   98
MKAN-724     .......... .......... .......... .......... ....GCCG..   98
MKAN-18494   .......... .......... .......... .......... ....GCCG..   98
MKAN-711     .......... .......... .......... .......... ....GCCG..   98
MKAN-725     .......... .......... .......... .......... ....GCCG..   98
```

Figure 4B:
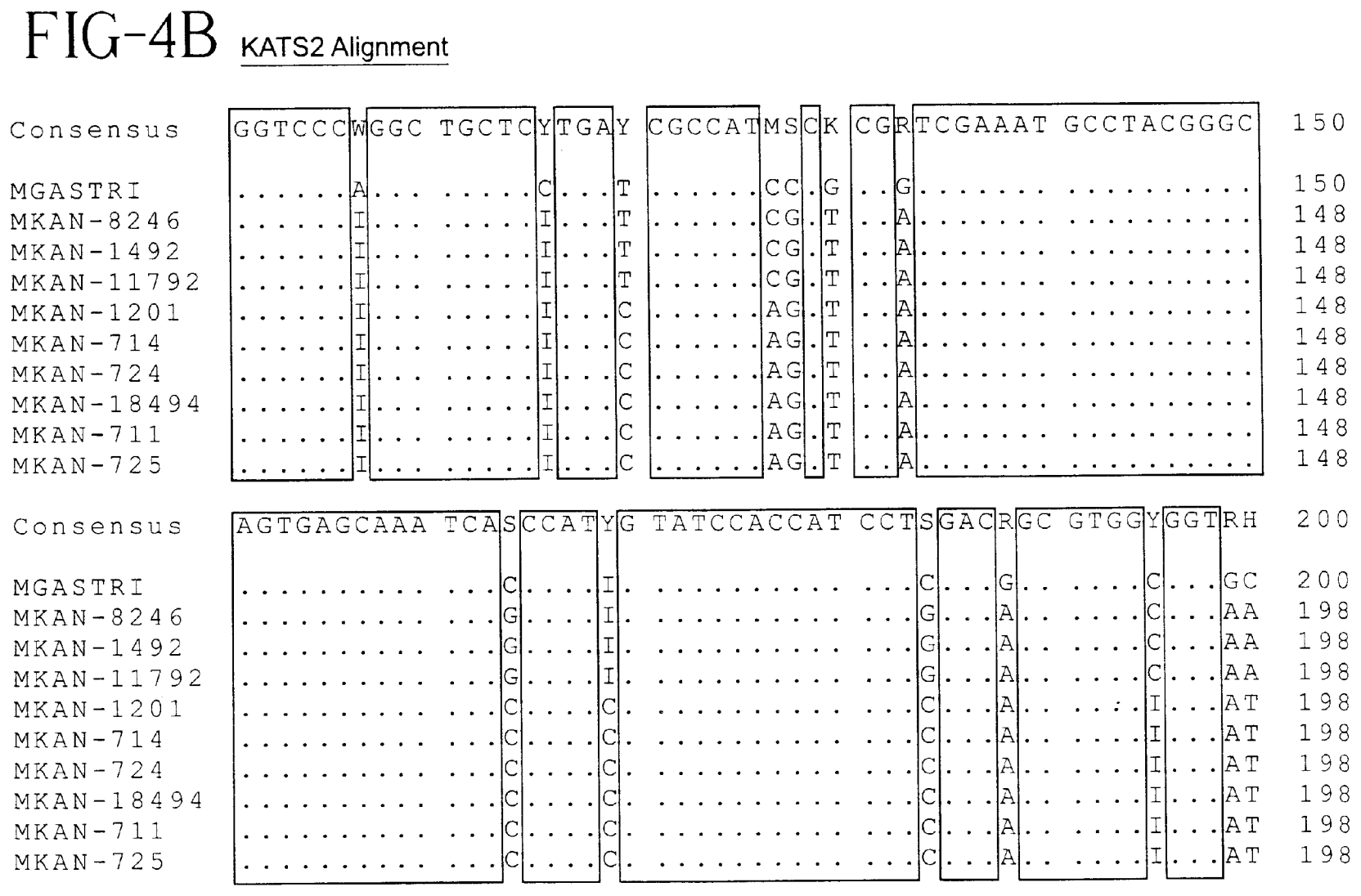

FIG-4B KATS2 Alignment

```
Consensus    GGTCCCWGGC TGCTCYTGAY CGCCATMSCK CGRTCGAAAT GCCTACGGGC  150

MGASTRI      ......A... .....C...T ......CC.G ..G....... ..........  150
MKAN-8246    ......T... .....T...T ......CG.T ..A....... ..........  148
MKAN-1492    ......T... .....T...T ......CG.T ..A....... ..........  148
MKAN-11792   ......T... .....T...T ......CG.T ..A....... ..........  148
MKAN-1201    ......T... .....T...C ......AG.T ..A....... ..........  148
MKAN-714     ......T... .....T...C ......AG.T ..A....... ..........  148
MKAN-724     ......T... .....T...C ......AG.T ..A....... ..........  148
MKAN-18494   ......T... .....T...C ......AG.T ..A....... ..........  148
MKAN-711     ......T... .....T...C ......AG.T ..A....... ..........  148
MKAN-725     ......T... .....T...C ......AG.T ..A....... ..........  148

Consensus    AGTGAGCAAA TCASCCATYG TATCCACCAT CCTSGACRGC GTGGYGGTRH  200

MGASTRI      .......... ...C....T. .......... ...C...G.. ....C...GC  200
MKAN-8246    .......... ...G....T. .......... ...G...A.. ....C...AA  198
MKAN-1492    .......... ...G....T. .......... ...G...A.. ....C...AA  198
MKAN-11792   .......... ...G....T. .......... ...G...A.. ....C...AA  198
MKAN-1201    .......... ...C....C. .......... ...C...A.. ....T...AT  198
MKAN-714     .......... ...C....C. .......... ...C...A.. ....T...AT  198
MKAN-724     .......... ...C....C. .......... ...C...A.. ....T...AT  198
MKAN-18494   .......... ...C....C. .......... ...C...A.. ....T...AT  198
MKAN-711     .......... ...C....C. .......... ...C...A.. ....T...AT  198
MKAN-725     .......... ...C....C. .......... ...C...A.. ....T...AT  198
```

FIG-4C

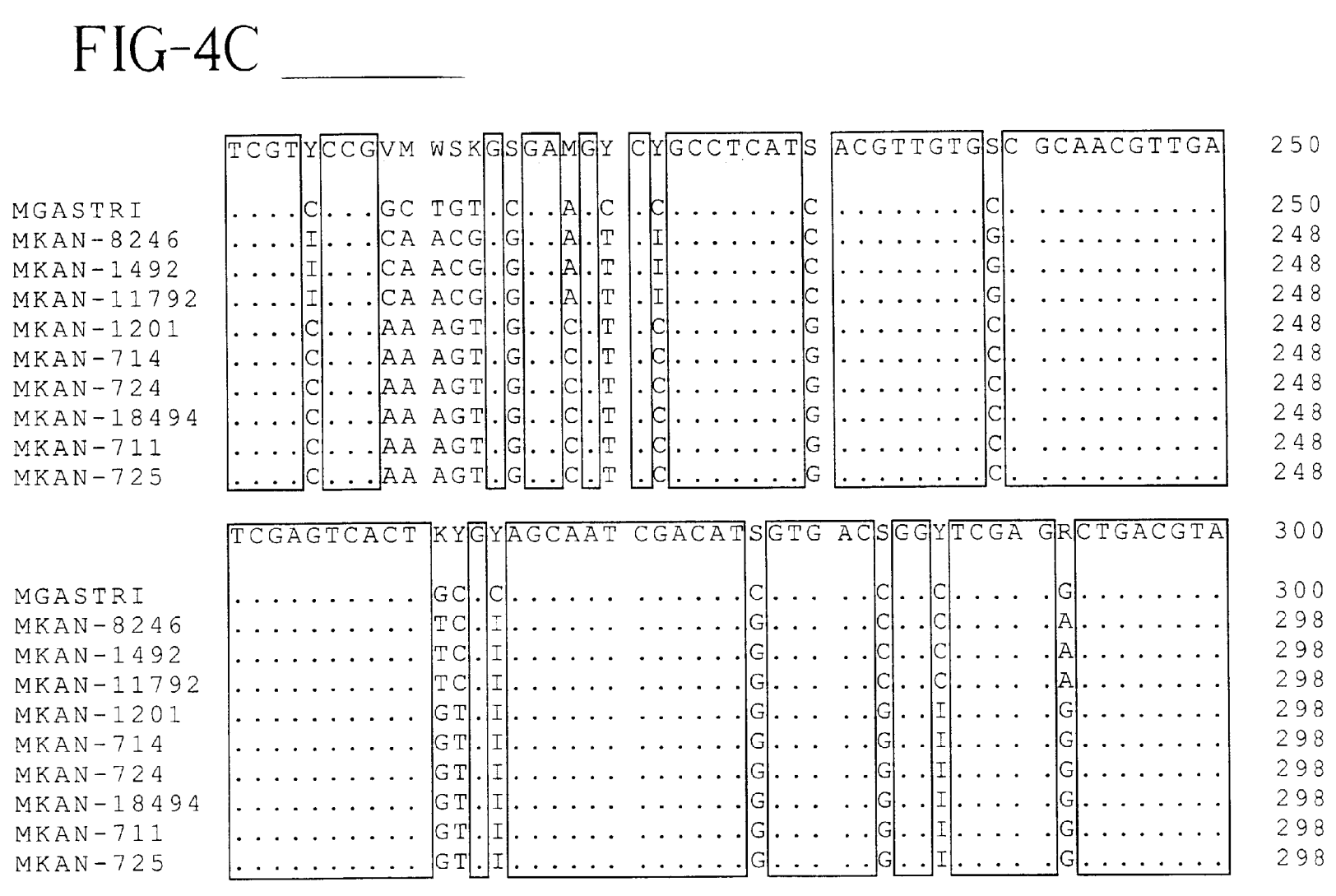

```
             TCGTYCCGVM WSKGSGAMGY CYGCCTCATS ACGTTGTGSC GCAACGTTGA  250
MGASTRI      ....C...GC TGT.C..A.C .C........C .........C. ..........  250
MKAN-8246    ....T...CA ACG.G..A.T .T........C .........G. ..........  248
MKAN-1492    ....T...CA ACG.G..A.T .T........C .........G. ..........  248
MKAN-11792   ....T...CA ACG.G..A.T .T........C .........G. ..........  248
MKAN-1201    ....C...AA AGT.G..C.T .C........G .........C. ..........  248
MKAN-714     ....C...AA AGT.G..C.T .C........G .........C. ..........  248
MKAN-724     ....C...AA AGT.G..C.T .C........G .........C. ..........  248
MKAN-18494   ....C...AA AGT.G..C.T .C........G .........C. ..........  248
MKAN-711     ....C...AA AGT.G..C.T .C........G .........C. ..........  248
MKAN-725     ....C...AA AGT.G..C.T .C........G .........C. ..........  248

             TCGAGTCACT KYGYAGCAAT CGACATSGTG ACSGGYTCGA GRCTGACGTA  300
MGASTRI      .......... GC.C...... .......C.. ..C..C.... .G........  300
MKAN-8246    .......... TC.T...... .......G.. ..C..C.... .A........  298
MKAN-1492    .......... TC.T...... .......G.. ..C..C.... .A........  298
MKAN-11792   .......... TC.T...... .......G.. ..C..C.... .A........  298
MKAN-1201    .......... GT.T...... .......G.. ..G..T.... .G........  298
MKAN-714     .......... GT.T...... .......G.. ..G..T.... .G........  298
MKAN-724     .......... GT.T...... .......G.. ..G..T.... .G........  298
MKAN-18494   .......... GT.T...... .......G.. ..G..T.... .G........  298
MKAN-711     .......... GT.T...... .......G.. ..G..T.... .G........  298
MKAN-725     .......... GT.T...... .......G.. ..G..T.... .G........  298
```

FIG-4D KATS2 Alignment

| | | |
|---|---|---|
| Consensus | ACGRTTYTCG G | 311 |
| MGASTRI | ...G..C.... . | 311 |
| MKAN-8246 | ...A..I.... . | 309 |
| MKAN-1492 | ...A..I.... . | 309 |
| MKAN-11792 | ...A..I.... . | 309 |
| MKAN-1201 | ...G..C.... . | 309 |
| MKAN-714 | ...G..C.... . | 309 |
| MKAN-724 | ...G..C.... . | 309 |
| MKAN-18494 | ...G..C.... . | 309 |
| MKAN-711 | ...G..C.... . | 309 |
| MKAN-725 | ...G..C.... . | 309 |

IDENTIFICATION OF A DNA REGION POTENTIALLY USEFUL FOR THE DETECTION OF *MYCOBACTERIUM KANSASII*

FIELD OF THE INVENTION

The present invention relates to methods and nucleic acid sequences for detecting and/or identifying microorganisms, in particular methods and nucleic acid sequences for detecting and/or identifying *M. kansasii* by nucleic acid amplification and nucleic acid hybridization.

BACKGROUND OF THE INVENTION

The mycobacteria are a genus of bacteria that are characterized as acid-fast, non-motile, gram-positive bacillus. The genus comprises many species including *Mycobacterium africanum, M. avium, M. bovis, M. bovis-BCG, M. chelonae, M. fortuitum, M. gordonae, M. intracellulare, M. kansasii, M. leprae, M. microti, M. scrofulaceum, M. paratuberculosis*, and *M. tuberculosis*. Some of the mycobacteria are pathogenic to both humans and animals, in particular *M. tuberculosis, M. leprae*, and *M. bovis*. Other mycobacterial species are not normally pathogenic, but cause opportunistic infections in immunocompromised individuals, such as AIDs patients. For example, infection by *M. kansasii, M. avium*, and *M. intracellulare* can cause severe lung disease in subjects in whom the immune system is suppressed or compromised. In fact, for the first time since 1953, reported cases of mycobacterial infections are increasing in the United States; many of these cases are related to the AIDS epidemic.

Conventional laboratory diagnosis of mycobacteria is based on acid-fast staining and cultivation of the organism, followed by biochemical assays. As a result of the slow growth and long generation time of mycobacteria, accurate laboratory diagnosis of mycobacteria by conventional techniques can take as long as six weeks. Automated culturing systems such as the BACTEC™ system (Becton Dickinson Microbiology Systems, Sparks, Md.) can decrease the time for identification of mycobacteria to one to two weeks. Nevertheless, there still exists a need in the art to reduce the time required for accurate diagnosis of mycobacteria to less than a week, preferably to about one day.

Nucleic acid based diagnostic assays, such as Southern hybridization, offer rapid results, usually in less than one day. PCR-based methods for identifying mycobacteria are even more sensitive and can often provide results within hours. However, nucleic acid based methodologies for diagnosing mycobacteria are often fraught with drawbacks. Most of these methods are costly, are available for only a few species of mycobacteria, and can resolve only one species per sample tested. Moreover, nucleic acid based assays require the development of oligonucleotide probes or primers that are specific for the genus Mycobacterium or for a particular species of mycobacteria.

Conventional laboratory identification of the mycobacterial species *M. kansasii* is based upon growth characteristics and biochemical testing. The biochemical profile of *M. kansasii* includes catalase production, urease activity, TWEEN™ hydrolysis, nitrate reduction, and photochromogenicity (i.e., the bacterium produces pigment when exposed to light). Several other species of mycobacterium show similar biochemical properties to *M. kansasii*, and photochromogenicity is usually relied upon for conclusive identification of *M. kansasii*. Determination of photochromogenicity is often problematic because it requires a pure organism culture, and this trait is variable, subjective and difficult to determine reliably.

To obviate the problems attendant to conventional diagnosis of *M. kansasii*, there have been attempts to develop nucleic acid based diagnostic methods using species-specific hybridization or nucleic acid amplification with *M. kansasii*-specific oligonucleotide primers.

Z. H. Huang et al. (*J. Clin. Microbiol.* 29, 2125 (1991)) disclose a DNA probe (pMK1-9) from a *M. kansasii* genomic library. The pMK1-9 probe hybridizes to *M. kansasii* DNA, but it also cross-hybridizes with other species of mycobacteria. In addition, this probe fails to detect one genetically distinct sub-group of *M. kansasii*. Huang et al. did not report the nucleotide sequence of pMK1-9, nor was the gene from which it was derived identified. B. C. Ross et al. (*J. Clin. Microbiol.* 30, 2930 (1992)) concerns the identification of *M. kansasii* using the pMK1-9 probe and a commercial DNA probe that specifically hybridized to the *M. kansasii* rRNA gene (ACCU-PROBE™, Gen-Probe, San Diego, Calif.). Ross et al. reported that both the pMK1-9 probe and the ACCU-PROBE™ failed to detect a significant number of *M. kansasii* strains. Tortoli et al. (*Eur. J. Clin. Microbiol. Infect. Dis.* 13, 264 (1994)) also evaluated the efficacy of using the ACCU-PROBE™ to detect *M. kansasii*. These investigators found the ACCU-PROBE™ was 100% species-specific, showing no cross-reactivity with other mycobacterial species, but it only detected 73% of the *M. kansasii* strains tested, possibly as a result of the genetic heterogeneity among the strains.

M. Yang et al. (*J. Clin. Microbiol.* 31, 2769 (1993)) derived an *M. kansasii* specific DNA hybridization probe (p6123) from a clinical isolate of *M. kansasii*. The p6123 probe hybridized to all *M. kansasii* strains tested, including the sub-group that Ross et al. (supra) found to be pMK1-9 negative. U.S. Pat. No. 5,500,341 to Spears discloses *M. kansasii*-specific amplification primers derived from the p6123 probe.

B. Böddinghaus et al. (*J. Clin. Microbiol.* 28, 1751 (1990)) disclose Mycobacterium genus-specific oligonucleotides derived from 16S rRNA sequences that specifically amplify and hybridize to mycobacterial DNA.

T. Rogall et al. (*J. Gen. Microbiol.* 136, 1915 (1990)) used PCR amplification of a region of the 16S rRNA gene followed by direct sequencing to identify various mycobacterial species. However, this method could not distinguish *M. kansasii* from *M. gastri* because the sequences of the 16S rRNA gene in these two species is identical, despite their differing phenotypic characteristics.

Hughes et al. (*J. Clin. Microbiol.* 31, 3216 (1993)) used PCR to amplify the 16S rRNA gene followed by either restriction enzyme analysis or direct cycle sequencing to identify various mycobacterial species. Hughes et al. also found that these methods could not differentiate between *M. kansasii* and *M. gastri*. Kirschner et al. (*J. Clin. Microbiol.* 31, 2882 (1993)) reported similar results. Kirschner et al. also disclose that *M. kansasii* and *M. gastri* can be distinguished by supplementing the nucleic acid based diagnostic methods with a photochromogenecity test. Id. at 2885.

M. Vaneechoutte et al., (*J. Clin. Microbiol* 31, 2061 (1993)) teaches a method of identifying specific mycobacterial species, including *M. kansasii*, by PCR amplification of the 16S rDNA combined with restriction analysis of the amplification products. This technique allows the positive identification of *M. kansasii* within one day. Vaneechoutte et al. did not evaluate whether this technique could identify *M. gastri* or whether it could distinguish *M. kansasii* from *M. gastri*.

Accordingly, there remains a need in the art for rapid, accurate and sensitive methods of identifying *M. kansasii*.

SUMMARY OF THE INVENTION

The present invention provides a newly-identified fragment of the *M. kansasii* genome which can be used to detect *M. kansasii* nucleic acid by hybridization or amplification assays.

As a first aspect, the present invention provides a method for detecting *Mycobacterium kansasii* comprising: (a) hybridizing a nucleic acid probe to *Mycobacterium kansasii* nucleic acids, preferably, the probe comprising at least 10 consecutive nucleotides of a *Mycobacterium kansasii* KATS2 sequence, and (b) detecting hybridization between the nucleic acid probe and the *Mycobacterium kansasii* nucleic acids.

As a second aspect, the present invention provides a method for species-specific detection of *Mycobacterium kansasii* comprising: (a) hybridizing a nucleic acid probe to *Mycobacterium kansasii* nucleic acids, preferably, the probe comprising at least 10 consecutive nucleotides of a *Mycobacterium kansasii* KATS2 sequence, and (b) detecting hybridization between the nucleic acid probe and the *Mycobacterium kansasii* nucleic acids.

As a third aspect, the present invention discloses a method for detecting *Mycobacterium kansasii* comprising: (a) hybridizing an amplification primer comprising a target binding sequence to *Mycobacterium kansasii* nucleic acids, preferably, the target binding sequence comprising at least 10 consecutive nucleotides of a *Mycobacterium kansasii* KATS2 sequence, and (b) amplifying the *Mycobacterium kansasii* nucleic acids, and (c) detecting the amplified *Mycobacterium kansasii* nucleic acids.

As a fourth aspect, the present invention provides a method for species-specific detection of *Mycobacterium kansasii* comprising: (a) hybridizing an amplification primer comprising a target binding sequence to *Mycobacterium kansasii* nucleic acids, preferably, the target binding sequence comprising at least 10 consecutive nucleotides of a *Mycobacterium kansasii* KATS2 sequence, (b) amplifying the *Mycobacterium kansasii* nucleic acids, and (c) detecting the amplified *Mycobacterium kansasii* nucleic acids.

As a fifth aspect, the present invention discloses isolated DNA comprising a *Mycobacterium kansasii* KATS2 sequence. The present invention further provides an oligonucleotide, preferably comprising at least 10 consecutive nucleotides of a *Mycobacterium kansasii* KATS2 sequence, where the oligonucleotide does not hybridize to non-*Mycobacterium kansasii* nucleic acids under stringent conditions, preferably defined by a wash stringency of 0.3 M NaCl, 0.03 M sodium citrate, 0.1% SDS at 60° C.

As a sixth aspect, the present invention provides a kit for detecting *Mycobacterium kansasii* nucleic acids comprising: (a) an inventive oligonucleotide according to the present invention, and (b) means for detecting the *Mycobacterium kansasii* nucleic acids using the oligonucleotide. Further disclosed is a kit for species-specific detection of *Mycobacterium kansasii* nucleic acids.

These and other aspects of the present invention are set forth in more detail in the description of the invention below.

BRIEF DESCRIPTION OF THE DRAWINGS

FIG. 1 presents the sequence of one strand of the double-stranded KATS2 DNA fragment (strain 1201; SEQ ID NO:4) amplified by AP-PCR from genomic DNA from a typical strain of *M. kansasii*. The sequence is shown in the 5' to 3' direction. The BsoB1 recognition site (CTCGGG) is shown in bold italics. Localization of KATS2 specific primers (E1C—SEQ ID NO:5; E3—SEQ ID NO:9; I2—SEQ ID NO:8; I4—SEQ ID NO:6 and I5—SEQ ID NO:7) is indicated. The E3, I2 and I5 primers hybridize to the DNA strand opposite of that shown.

FIG. 2 presents the DNA sequence of one strand of the KATS2 region from an atypical strain of *M. kansasii* (strain 1492; SEQ ID NO:10). The BsoB1 recognition site (CTCGGG) is shown in bold italics. The primers are as indicated in the description of FIG. 1.

FIG. 3 shows the alignment of the KATS2 sequences from typical and atypical strains of *M. kansasii* (SEQ ID NO:4, SEQ ID NO:10 to SEQ ID NO:17) to generate a consensus KATS2 sequence (top sequence, SEQ ID NO:18).

FIG. 3A shows nucleotides 1 through 200 of the aligned and consensus KATS2 sequences.

FIG. 3B shows nucleotides 201 through 309 of the aligned and consensus KATS2 sequences.

FIG. 4 shows the alignment of the KATS2 sequences from typical and atypical strains of *M. kansasii* (SEQ ID NO:4, SEQ ID NO:10 to SEQ ID NO:17) with the KATS2 sequence of *M. gastri* (SEQ ID NO:20) to generate a consensus *M. kansasii/M. gastri* KATS2 sequence (top sequence, SEQ ID NO:19).

FIG. 4A shows nucleotides 1 through 198 or 200 of the aligned and consensus KATS2 sequences.

FIG. 4B shows nucleotides 199 or 201 through 309 or 311 of the aligned and consensus KATS2 sequences.

DETAILED DESCRIPTION OF THE INVENTION

Nucleotide sequences are presented herein by single strand only in the 5' to 3' direction, from left to right. Nucleotides are represented herein in the manner recommended by the IUPAC-IUB Biochemical Nomenclature Commission, in accordance with 37 C.F.R. § 1.822 and established usage.

The production and use of cloned genes, recombinant DNA, vectors, transformed host cells, selectable markers, proteins, and protein fragments by genetic engineering are well-known to those skilled in the art. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59. All United States patent references cited herein are intended to be incorporated in their entirety by reference.

Disclosed herein are the nucleotide sequences of a region of the *M. kansasii* DNA, designated "KATS2", from numerous typical and atypical strains of *M. kansasii*. The KATS2 region exhibits a high degree of sequence similarity among typical and atypical *M. kansasii* strains. The KATS2 sequences disclosed herein find use in methods of detecting and diagnosing *M. kansasii*. For example, these sequences can be used to design hybridization probes for use in conventional Southern or dot blot hybridizations or to design amplification primers for use in Polymerase Chain Reaction (PCR), Ligase Chain Reaction (LCR), Strand Displacement Amplification (SDA), or thermophilic Strand Displacement Amplification (tSDA).

The KATS2 sequences disclosed herein include the sequences given as SEQ ID NO:4 and SEQ ID NO:10 to SEQ ID NO:17, and the complements thereof KATS2 sequences from strains of *M. kansasii*, both typical and atypical strains, other than those specifically disclosed herein are also an aspect of the present invention. Alternatively stated, KATS2 sequences of the present invention include the amplification products (i.e., amplicons) resulting from amplification of *M. kansasii* nucleic acids as template with KATS2 amplification primers, such as E1C (SEQ ID NO:5) and E3 (SEQ ID NO:9). KATS2 sequences from strains of *M. kansasii* other than those specifically disclosed herein will generally be at least about 75% homologous (and more preferably 80%, 85%, 90% or even 95% homologous) to a continuous segment of DNA found within the *M. kansasii* KATS2 regions having sequences given herein as SEQ ID NO:4 and SEQ ID NO:10 to SEQ ID NO:17, and will be able to hybridize to *M. kansasii* nucleic acids under conditions of high stringency, as defined below.

The KATS2 sequences of the present invention include sequences that hybridize under conditions of high stringency to *M. kansasii* nucleic acids and are substantially homologous to the KATS2 sequences specifically disclosed herein, and particularly the KATS2 sequences disclosed herein as SEQ ID NO:4 and SEQ ID NO:10 to SEQ ID NO:17. This definition is intended to encompass natural allelic variations in the KATS2 sequence. As used herein, nucleotide sequences that are "substantially homologous" are at least 75%, and more preferably are 80%, 90% or even 95% homologous.

High stringency hybridization conditions that will permit homologous DNA sequences to hybridize to a DNA sequence as given herein are well known in the art. For example, hybridization of such sequences to DNA disclosed herein may be carried out in 25% formamide, 5× SSC, 5× Denhardt's solution, with 100 μg/ml of single stranded DNA, and 5% dextran sulfate at 42° C., with wash conditions of 25% formamide, 5× SSC, 0.1% SDS at 42° C. for 15 minutes, to allow hybridization of sequences of about 60% homology. More stringent conditions are represented by a wash stringency of 0.3 M NaCl, 0.03 M sodium citrate, 0.1% SDS at 60° C., or even 70° C. See SAMBROOK ET AL., MOLECULAR CLONING, A LABORATORY MANUAL (2d ed. 1989). In general, KATS2 sequences which hybridize to the KATS2 regulatory elements disclosed herein will be at least 75%, 80%, 85%, 90% or even 95% homologous or more with the KATS2 sequences disclosed herein.

Nucleic acid hybridization probes are also aspects of the present invention. As used herein, the term "probe" indicates an oligonucleotide that hybridizes to a target nucleotide sequence, typically to facilitate its detection. Unlike a primer, a probe is not extended by a polymerase. The probe is often linked to a detectable label to facilitate its detection or capture when hybridized to the target sequence, thus facilitating detection of the target sequence. As used herein, the "target sequence" of a hybridization probe refers to a nucleic acid sequence to which the probe specifically binds.

The probes disclosed herein hybridize to *M. kansasii* nucleic acids. Typically, the probes of the present invention will hybridize to consecutive nucleotides of the KATS2 sequences disclosed herein under stringent conditions, as defined above. Alternatively stated, probes of the present invention will be at least 75%, 80%, 85%, 90% or even 95% homologous or more with consecutive nucleotides within the KATS2 sequences disclosed herein, in particular SEQ ID NO:4 and SEQ ID NO:10 to SEQ ID NO:17. In particular embodiments of the invention, the probes have nucleotide sequences as given herein as SEQ ID NO:5 to SEQ ID NO:9, and complements thereof. As nucleic acids do not require complete homology to hybridize, it will be apparent to those skilled in the art that the probe sequences specifically disclosed herein may be modified so as to be substantially homologous to the probe sequences disclosed herein without loss of utility as *M. kansasii* probes. It is well-known in the art that hybridization of homologous and partially homologous nucleic acid sequences may be accomplished by adjusting the hybridization conditions to increase or decrease the stringency (i.e., adjusting the hybridization temperature or salt content of the buffer).

Nucleic acid hybridization probes can be of any suitable length. There is no particular lower or upper limits to the length of the probe, as long as the probes hybridize to the target KATS2 nucleic acids and function effectively as a probe (e.g., they facilitate detection). In one preferred embodiment of the invention the probe comprises at least 10 consecutive nucleotides of a *M. kansasii* KATS2 sequence, as defined above. The probes of the present invention can be as short as 50, 40, 30, 20, 15, or 10 nucleotides, or shorter. Likewise, the probes can be as long as 20, 40, 50, 60, 75, 100 or 200 nucleotides, or longer. The maximum length of the probe is the length of the particular KATS2 sequence selected. For example, a probe derived from the *M. kansasii* strain 711 KATS2 sequence (see FIG. 3; SEQ ID NO:11) can be as long as 309 nucleotides. However, for convenience, probes are typically 10–200 nucleotides long, preferably 12–100 nucleotides long, more preferably 15–100 nucleotides long, or most preferably 15–75 nucleotides long.

In a preferred embodiment of the invention, the oligonucleotide probe does not hybridize under stringent conditions, as defined above (e.g., a wash stringency of 0.3 M NaCl, 0.03 M sodium citrate, 0.1% SDS at 60° C.), to nucleic acids from any genus other than Mycobacteria, or does so to only a negligible extent such that there is only insubstantial hybridization or detection of non-Mycobacteria nucleic acids under the same conditions in which the probe does hybridize to and detect Mycobacteria nucleic acids. In a more preferred embodiment, the probe does not hybridize under stringent conditions to nucleic acids from species of Mycobacteria other than *M. kansasii* and *M. gastri* nucleic acids, or does so to a negligible extent such that there is only insubstantial hybridization or detection of non-*M. kansasii* or non-*M. gastri* nucleic acids under the same conditions in which the probe does hybridize to and detect *M. kansasii* and *M. gastri* nucleic acids. In a further preferred embodiment, the probe does not hybridize to *M. gastri* nucleic acids, or does so to a negligible extent such that there is only insubstantial hybridization or detection of *M. gastri* nucleic acids under the same conditions in which the probe does hybridize to and detect *M. kansasii* nucleic acids. In a yet further preferred embodiment, the probe is species-specific, meaning it only hybridizes under stringent conditions to nucleic acids from *M. kansasii* and does not hybridize to nucleic acids from any other mycobacterial or non-mycobacterial species, or does so to a negligible extent such that there is only insubstantial hybridization or detection of non-*M. kansasii* nucleic acids under the same conditions in which the probe does hybridize to and detect *M. kansasii* nucleic acids.

One aspect of the present invention is a method for detecting *M. kansasii* using a nucleic acid probe, as defined above. According to this embodiment of the invention, a nucleic acid probe is hybridized to *M. kansasii* nucleic acids, and the hybridization between the probe and the *M. kansasii* nucleic acids is then detected. Hybridization can be carried out under any suitable technique known in the art. Typically, hybridizations will be performed under conditions of high stringency. It will be apparent to those skilled in the art that hybridization conditions can be altered to increase or decrease the degree of hybridization, the level of specificity of the hybridization, and the background level of non-specific binding (i.e., by altering hybridization or wash salt concentrations or temperatures).

Similarly, detection of hybridization between the probe and the *M. kansasii* nucleic acids can be carried out by any method known in the art. The probe may contain a detectable label that will indicate hybridization between the labeled probe and the *M. kansasii* nucleic acids. The detectable label of the probe is a moiety that can be detected either directly or indirectly. For direct detection of the label, probes may be tagged with a radioisotope and detected by autoradiography. Alternatively, the probe may be tagged with a fluorescent moiety and detected by fluorescence as is known in the art. As a further alternative, the probe may be indirectly detected by tagging with a label that requires additional reagents to render it detectable. Illustrative methods of indirect labeling include those utilizing chemiluminescence agents, enzymes that produce visible reaction products, and ligands (e.g., haptens, antibodies or antigens) that may be detected by binding to labeled specific binding partners (e.g., hapten binding to a labeled antibody). Ligand labels are also useful for solid phase capture of the oligonucleotide probe (i.e., capture probes). Exemplary labels include biotin (detectable by binding to labeled avidin or streptavidin) and enzymes, such as horseradish peroxidase or alkaline phosphatase (detectable by addition of enzyme substrates to produce a colored reaction product). Methods of labeling oligonucleotides are well known in the art.

A preferred embodiment of the invention is a species-specific method of detecting *M. kansasii* using a nucleic acid probe. By "species-specific method of detecting *M. kansasii*," it is meant that the probe does not substantially hybridize to and detect non-*M. kansasii* nucleic acids under the same conditions in which the probe does hybridize to *M. kansasii* nucleic acids, as described above. In particular, the probe does not hybridize to and detect nucleic acids from *M. gastri*, or hybridizes minimally at a level distinguishable from hybridization to *M. kansasii* nucleic acids, under the same conditions in which the probe does hybridize to *M. kansasii* nucleic acids, as described above. In addition, the probe does not hybridize to or detect nucleic acids from other species closely related to *M. kansasii*, such as *Rhodococcus rhodochrous* and *Nocardia asteroides* under the same conditions in which the probe does hybridize to *M. kansasii* nucleic acids, as described above. Alternatively stated, the term "species-specific" refers to oligonucleotide hybridization or detection in a species of organism or a group of related species without substantial oligonucleotide hybridization or detection in other species of the same genus or species of a different genus. Specifically, as used herein, a species-specific method of detecting *M. kansasii* using a nucleic acid probe indicates that the probe hybridizes to and detects *M. kansasii* nucleic acids under stringent conditions, but it does not hybridize to and detect under stringent conditions non-*M. kansasii* nucleic acids, in particular nucleic acids from non-Mycobacteria species, nucleic acids from other species of Mycobacteria, and nucleic acids from species closely related to *M. kansasii*, such as *Rhodococcus rhodochrous* and *Nocardia asteroides.*

Another aspect of the present invention is amplification primers. An amplification primer is an oligonucleotide for amplification of a target sequence by extension of the oligonucleotide after hybridization to the target sequence or by ligation of multiple oligonucleotides that are adjacent when hybridized to the target sequence. Copies of the target sequence which are generated during the amplification reaction are referred to as "amplification products", "amplimers", or "amplicons". An extension product refers to the copy of a target sequence produced by hybridization of a primer and extension of the primer by polymerase using the target sequence as a template.

As used herein, the "target sequence" of an amplification primer refers to a nucleic acid sequence to which the amplification primer specifically binds and amplifies. These include the original nucleic acid sequence to be amplified and its complementary second strand as well as either strand of a copy of the original target sequence generated during the amplification reaction.

An SDA amplification primer comprises a target binding sequence, a recognition site for a restriction endonuclease, and a tail. The target binding sequence is at the 3' end of the SDA amplification primer. It hybridizes to the 3' end of the target sequence. Generally, the total length for an SDA amplification primer is 20–75 nucleotides, preferably 25–50 nucleotides. The target binding sequence confers hybridization specificity on the amplification primer. A recognition site for a restriction endonuclease is 5' of the target binding sequence. The recognition site is for a restriction endonuclease that will nick one strand of a DNA complex when the recognition site is hemimodified, as described by G. Walker et al. *Proc. Nat'l Acad. Sci. USA* 89, 392 (1992); *Nucl. Acids. Res.* 20, 1691 (1992). The tail of the amplification primer is comprised of nucleotides 5' of the restriction endonuclease recognition site. The tail and a portion of the restriction endonuclease recognition site function as a polymerase repriming site when the remainder of the amplification primer is nicked and displaced during SDA. The repriming function of the tail sustains the SDA reaction and allows synthesis of multiple amplicons from a single target molecule. The tail is generally quite short. Its length and sequence are generally not critical and may be routinely selected and modified to obtain stable hybridization of the tail region and any remaining portion of the restriction endonuclease recognition site to the target after nicking of the amplification primer. One consideration is that the tail generally should not contain sequences that will hybridize either to the target binding sequence or to other primers.

The KATS2 sequences disclosed herein contain an internal recognition site for the restriction endonuclease BsoB1. See FIG. 1 and FIG. 2. BsoB1 is a commonly used restriction endonuclease for thermophilic SDA (tSDA). Amplification of KATS2 by SDA or tSDA can be carried out using another restriction endonuclease, such as HincII, HindII, Nci I, and Fnu4H1 that are compatible with SDA or BsrI, BstNI, BsmAI and BslI that are compatible with the tSDA system. Such restriction endonucleases are known to those skilled in the art. See, e.g., G. Walker et al. *Proc. Nat'l. Acad. Sci. USA* 89, 392 (1992) at page 394, U.S. Pat. No. 5,455,166 and European Patent No. 0 684 315 A1. Preferably, the recognition site is for a thermophilic restriction endonuclease so that tSDA may be employed, thereby achieving greater specificity and efficiency of amplification. Alternatively, the amplification primers can both be directed to target sequences lying either 5' or 3' of the BsoB1 site in the KATS2 sequence, such that the BsoB1 recognition site is not amplified. For example, the approximately 250 bp fragment from the internal BsoB1 site to the 3' end of the KATS2 sequence can be amplified by SDA or tSDA amplification. FIG. 1; SEQ ID NO:4.

As used herein, a "bumper primer" or "external primer" is a primer used to displace primer extension products in SDA and tSDA amplification reactions. The bumper primer hybridizes to a target sequence upstream of the amplification primer target binding sequence such that extension of the bumper primer displaces the downstream amplification primer and its extension product. It will not usually be necessary that the bumper primers used in SDA and tSDA reactions be specific to *M. kansasii* or the genus Mycobacteria. The bumper primers are only required to hybridize to its target upstream from the amplification primers so that when the bumper primers are extended they will displace the amplification primer and its extension product. The sequence of the bumper primers is therefore generally not critical, and may be derived from any upstream target sequence that is sufficiently close to the binding site of the amplification primer to allow displacement of the amplification primer extension product upon extension of the bumper primer. Occasional mismatches with the target in the bumper primer sequence or some cross-hybridization with non-target sequences do not generally have a negative affect on amplification efficiency as long as the bumper primer still hybridizes to the specific target sequence. In one embodiment of the present invention, the bumper primers comprise at least 10 consecutive nucleotides of a KATS2 sequence or the complement thereof, but are typically similar in size to probes as described above. Bumper primers according to this embodiment may also be used as the target binding sequence of an amplification primer or as a probe.

For amplification methods that do not require specialized sequences at the ends of the target (e.g., PCR and LCR), the amplification primer typically consists essentially of only the target binding sequence. For amplification methods other than SDA that require specialized sequences in the amplification primer (e.g., an RNA polymerase promoter for Self-Sustained Sequence Replication (3SR; J. C. Guatelli et al., *Proc Natl. Acad. Sci. USA* 87, 1874–78 (1990)), Nucleic Acid Sequence-Based Amplification (NASBA; van der Vliet et al., *J. General Microbiol* 139, 2423–29 (1993)), or transcription based amplification (D. Y. Kwoh et al., *Proc. Natl. Acad. Sci. USA* 86, 1173–77 (1989)), the specialized sequence may be linked to the target binding sequence using routine methods for preparation of oligonucleotides without altering the hybridization specificity of the target binding sequence.

Thus, it will be apparent to those skilled in the art that primers and probes of the present invention in many cases are structurally similar or identical. The terms primer and probe refer to the function of the oligonucleotide. An oligonucleotide may function as a probe if it is hybridized to a target sequence to capture or detect the target sequence. Alternately, the same oligonucleotide may function as a primer if it is used to amplify the target, as described above.

Suitable bases for preparing the oligonucleotide probes or amplification primers of the present invention may be selected from naturally occurring nucleotide bases such as adenine, cytosine, guanine, uracil, and thymine; and non-naturally occurring or "synthetic" nucleotide bases such as 8-oxo-guanine, 6-mercaptoguanine, 4-acetylcytidine, 5-(carboxyhydroxyethyl)uridine, 2'-O-methylcytidine, 5-carboxymethylamino-methyl-2-thioridine, 5-carboxymethylaminomethyluridine, dihydrouridine, 2'-O-methylpseudouridine, β,D-galactosylqueosine, 2'-O-methylguanosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, β,D-mannosylqueosine, 5-methoxycarbonylmethyluridine, 5-methoxyuridine, 2-methylthio-N6-isopentenyladenosine, N-((9-β-D-ribofuranosyl-2-methylthiopurine-6-yl)carbamoyl) threonine, N-((9-β-D-ribofuranosylpurine-6-yl)N-methylcarbamoyl)threonine, uridine-5-oxyacetic acid methylester, uridine-5-oxyacetic acid, wybutoxosine, pseudouridine, queosine, 2-thiocytidine, 5-methyl-2-thiouridine, 2-thiouridine, 2-thiouridine, 5-methylurdine, N-((9-β-D-ribofuranosylpurine-6-yl)carbamoyl)threonine, 2'-O-methyl-5-methyluridine, 2'-O-methylurdine, wybutosine, and 3-(3-amino-3-carboxypropyl)uridine. Any oligonucleotide backbone may be employed, including DNA, RNA (although RNA is less preferred than DNA), modified sugars such as carbocycles, and sugars containing 2' substitutions such as fluoro and methoxy. The oligonucleotides may be oligonucleotides wherein at least one, or all, of the internucleotide bridging phosphate residues are modified phosphates, such as methyl phosphonates, methyl phosphonothioates, phosphoromorpholidates, phosphoropiperazidates and phosphoramidates (for example, every other one of the internucleotide bridging phosphate residues may be modified as described). The oligonucleotide may be a "peptide nucleic acid" such as described in P. Nielsen et al., *Science* 254, 1497–1500 (1991). The only requirement is that the oligonucleotide probe should possess a sequence at least a portion of which is capable of binding to a portion of the sequence of a target DNA molecule.

The amplification primers disclosed herein hybridize to *M. kansasii* nucleic acids. In general, such sequences will hybridize to consecutive nucleotides of the KATS2 sequences disclosed herein under stringent conditions, as defined above. Alternatively stated, primers of the present invention will be at least 75%, 80%, 85%, 90% or even 95% homologous or more with consecutive nucleotides within the KATS2 sequences disclosed herein, in particular SEQ ID NO:4 and SEQ ID NO:10 to SEQ ID NO:17. In particular embodiments of the invention, the primers have nucleotide sequences as given herein as SEQ ID NO:5 to SEQ ID NO:9, and complements thereof. As nucleic acids do not require complete homology to hybridize, it will be apparent to those skilled in the art that the primer sequences specifically disclosed herein may be modified so as to be substantially homologous to the primer sequences disclosed herein without loss of utility as *M. kansasii* amplification primers. It is well-known in the art that hybridization of homologous and partially homologous nucleic acid sequences may be accomplished by adjusting the hybridization conditions to increase or decrease the stringency (i.e., adjusting the hybridization temperature or salt content of the buffer).

Amplification primers can be of any suitable length. There is no particular lower or upper limits to the length of the primer, so long as the primer hybridizes to the target KATS2 DNA and functions effectively as an amplification primer. In one preferred embodiment of the invention the primers comprise at least 10 consecutive nucleotides of a *M. kansasii* KATS2 sequence, as defined above. The primers can be as short as 50, 40, 30, 20, 15, or 10 nucleotides, or shorter. Likewise, the primers can be as long as 20, 40, 50, 60, 75, 100 or 200 nucleotides, or longer.

In a preferred embodiment of the invention, the amplification primer does not hybridize to and amplify under stringent conditions, as defined above (e.g., a wash stringency of 0.3 M NaCl, 0.03 M sodium citrate, 0.1% SDS at 60° C.), nucleic acids from any genus other than those in the genus Mycobacteria, or does so to a negligible extent such that there is only insubstantial hybridization, amplification or detection of non-Mycobacteria nucleic acids under the same conditions in which the amplification primer does hybridize to, amplify and detect Mycobacteria nucleic acids. In a more preferred embodiment, the amplification primer does not hybridize to and amplify under stringent conditions nucleic acids from species of Mycobacteria other than *M. kansasii* and *M. gastri* nucleic acids, or does so to a negligible extent such that there is only insubstantial hybridization, amplification or detection of non-*M. kansasii* or non-*M. gastri* nucleic acids under the same conditions in which the amplification primer does hybridize to, amplify and detect *M. kansasii* and *M. gastri* nucleic acids. In a further preferred embodiment, the amplification primer does not hybridize to, amplify, or detect *M. gastri* nucleic acids, or does so to a negligible extent such that there is only insubstantial hybridization, amplification or detection of *M. gastri* nucleic acids under the same conditions in which the amplification primer does hybridize to, amplify and detect *M. kansasii* nucleic acids. In a yet further preferred embodiment, the amplification primer is species-specific, meaning it only hybridizes to and amplifies under stringent conditions nucleic acids from *M. kansasii* and does not hybridize to and amplify nucleic acids from any other mycobacterial or non-mycobacterial species, or does so to a negligible extent such that there is only insubstantial hybridization, amplification or detection of non-*M. kansasii* nucleic acids under the same conditions in which the amplification primer does hybridize to, amplify and detect *M. kansasii* nucleic acids.

Another aspect of the present invention is a method of detecting *M. kansasii* by hybridizing an amplification primer comprising a target binding sequence to *M. kansasii* nucleic acids, amplifying the *M. kansasii* nucleic acids, and then detecting the amplified *M. kansasii* nucleic acids. In one preferred embodiment of the invention, the amplification is carried out by extending the hybridized amplification primer to give an amplification product or amplicon, for example by Polymerase Chain Reaction (PCR). In another preferred embodiment, two amplification primers are hybridized to the *M. kansasii* nucleic acids and extended. Amplification reactions involving extension reactions include but are not limited to PCR, SDA, and tSDA.

Amplification reactions employing the primers of the present invention may incorporate thymine as disclosed by G. Walker et al. (*Proc. Nat'l Acad. Sci. USA* 89, 392 (1992); *Nucl. Acids. Res.* 20, 1691 (1992)), or they may wholly or partially substitute 2'-deoxyuridine 5'-triphosphate for TTP in the reaction to reduce cross-contamination with amplification products carried over from previous amplification reactions in reagents, pipetting devices and laboratory surfaces, for example, as is taught in European Patent No. 0 624 643. Deoxyuridine (dU) is incorporated into amplification products and can be excised by treatment with uracil DNA glycosylase (UDG). These abasic sites render any contaminating amplification product unamplifiable in subsequent amplification reactions. UDG may be inactivated by UDG inhibitor prior to performing the subsequent amplification to prevent excision of dU in newly-formed amplification products.

In another preferred embodiment of the invention, amplification is carried out by hybridizing two or more amplification primers to the *M. kansasii* nucleic acids, such that the primers are adjacent to each other when hybridized to their respective target sequences, and then ligating the hybridized amplification primers to produced a longer amplification product.

The presence of *M. kansasii* or *M. kansasii* nucleic acids are detected by determining the presence of the amplified *M. kansasii* nucleic acids. Amplification products can be detected by hybridization to a labeled probe as described above. When a probe is used to detect amplification, the probe is typically selected to hybridize to a sequence that lies between the amplification primers (i.e., an internal probe). When amplification is performed by LCR, a probe that overlaps both primers and does not detect unligated primers may be used. Alternatively, amplification products may be detected by their characteristic size, for example by electrophoresis followed by ethidium bromide staining to visualize the nucleic acids species. This is the preferred method of detecting amplification products for LCR methods. In a further alternative, a labeled amplification primer is used. In a still further alternative, a labeled amplification primer/internal probe is extended on the target sequence (a detector primer) for detection of amplification products as described by G. Walker et al. *Proc. Nat'l Acad. Sci. USA* 89, 392 (1992); *Nucl. Acids. Res.* 20, 1691 (1992).

Examples of specific detection methods that may be employed to detect amplification products include a chemiluminescent method in which amplified products are detected using a biotinylated capture probe and an enzyme-conjugated detector probe as described in U.S. Pat. No. 5,470,723. After hybridization of these two probes to different sites of the assay region of the target sequence (i.e., between the binding sites of the two amplification primers), the complex is captured on a streptavidin-coated microtiter plate, and the chemiluminescent signal is developed and read in a luminometer. As a further alternative method, a signal primer as described in European Patent No. 0 678 582 is included in the amplification reaction to facilitate detection of the amplification product. According to this embodiment, labeled secondary amplification products are generated during amplification in a target amplification-dependent manner and may be detected as an indication of target amplification by means of the associated label.

A further preferred embodiment of the invention is a species-specific method of detecting *M. kansasii* using an amplification primer. By "species-specific method of detecting *M. kansasii*," it is meant that the amplification primer does not hybridize to, amplify, and detect non-*M. kansasii* nucleic acids as described above under the same conditions in which the amplification primer does hybridize to, amplify and detect *M. kansasii* nucleic acids, as described above. In particular, the amplification primer does not hybridize to, amplify, and detect nucleic acids from *M. gastri* under the same conditions in which the amplification primer does hybridize to, amplify and detect *M. kansasii* nucleic acids, as described above. In addition, the amplification primer does not hybridize to, amplify, or detect nucleic acids from other species closely related to *M. kansasii*, such as *Rhodococcus rhodochrous* and *Nocardia asteroides* under the same conditions in which the amplification primer does hybridize to, amplify and detect *M. kansasii* nucleic acids, as described above. Alternatively stated, the term "species-specific" refers to oligonucleotide hybridization, amplification, or detection in a species of organism or a group of related species without substantial oligonucleotide hybridization, amplification, or detection in other species of the same genus or species of a different genus. Specifically, as used herein, a species-specific method of detecting *M. kansasii* using a nucleic acid amplification primer indicates that the amplification primer hybridizes to, amplifies, and detects *M. kansasii* nucleic acids under stringent conditions, but it does not hybridize to, amplify, and detect under stringent conditions non-*M. kansasii* nucleic acids, in particular nucleic acids from non-mycobacteria species, nucleic acids from other species of mycobacteria, nucleic acids from species closely related to *M. kansasii*, such as *Rhodococcus rhodochrous* and *Nocardia asteroides*, and nucleic acids from *M. gastri.*

The present invention also provides kits for detecting *M. kansasii* nucleic acids comprising a nucleic acid probe or amplification primer, preferably a pair of amplification primers, each as described hereinabove. Species-specific methods, probes and amplification primers for detecting *M. kansasii*, as described hereinabove, are preferred. The kit may additionally contain means for detecting the *M. kansasii* nucleic acids using the oligonucleotide nucleic acid or amplification primer, as described herein above. Preferably, the oligonucleotide probe or amplification primer comprises at least 10 consecutive nucleotides, more preferably not more than 50 consecutive nucleotides, of a *M. kansasii* KATS2 sequence. In an alternate embodiment, the amplification primer contains a sequence for amplification of a target nucleic acid in addition to a target binding sequence, each as described hereinabove. The kit may further include other components and reagents for performing the hybridization or amplification method (e.g., Southern hybridization, dot blot hybridization, PCR, SDA, etc., and the like). As an illustrative example, such a kit may contain at least one pair of amplification primers according to the present invention. For detection by hybridization, a hybridization solution such as 25% formamide, 5× SSC, 5× Denhardt's solution, 100 $\mu$g/ml of single stranded DNA, and 5% dextran sulfate, or other reagents known to be useful for probe hybridization may also be included. See SAMBROOK ET AL., MOLECULAR CLONING, A LABORATORY MANUAL (2d ed. 1989). Alternatively, reagents appropriate for use with one of the known nucleic acid amplification methods may be included with *M. kansasii* KATS2 amplification primers. The components of the kit are packaged together in a common container, typically including instructions for performing selected specific embodiments of the methods disclosed herein. Components for detection methods, as described hereinabove, may optionally be included in the kit, for example, a second probe, and/or reagents and means for performing label detection (e.g., radiolabel, enzyme substrates, antibodies, etc., and the like).

The methods, probes, amplification primers, and kits disclosed herein can be used to detect *M. kansasii* in any sample suspected of containing mycobacteria. The samples may comprise isolated nucleic acids, isolated microorganisms, or they may be clinical samples. Typically, clinical samples are in the form of a biological fluid or tissue (e.g., sputum, bronchial washings, gastric washings, blood, milk, lymph, skin, and soft tissues). As mycobacteria infect both human and non-human animal species, the present invention is applicable to both human and veterinary diagnostic procedures and the sample may be obtained from either source.

The following Examples are provided to illustrate the present invention and should not be construed as limiting thereof. As used herein, "ml" means milliliter, "$\mu$l" means microliter, "$\mu$M" means micromolar, "mM" means millimolar, "mg" means milligram, "ng" means nanogram, "min." means minute, "sec." means second, and "w/v" means weight/volume.

EXAMPLE 1

Isolation of a *M. kansasii* Specific DNA Fragment (KATS2)

Arbitrarily primed polymerase chain reaction (AP-PCR) was used to create a differential display of amplification products from typical (TMC1201) and atypical (LCDC724) *M. kansasii* strains, and the non-*M. kansasii* strains *M. tuberculosis* (H37Rv), *M. avium* (CDC33), and *M. intracellulare* (ATCC 13950). The primer for AP-PCR was 5'-CGTCATGCTGAAGTCCCT-3' (SEQ ID NO:1). The amplification reactions were carried out in 50 $\mu$l containing 10 mM TRIS-HCl, pH 8.3, 50 mM KCl, 1.5 mM MgCl2, 0.001% (w/v) gelatin, 0.2 mM dNTPs, 3.5 $\mu$M of each 32P-labeled primer, 2.5 units Taq DNA polymerase, and 1 ng genomic DNA from each organism as template. The AP-PCR was carried out in a Perkin Elmer Cetus thermocycler (Model 480). After denaturing the target DNA at 95° C. for 3 min., the amplification cycle was carried out 40 times as follows: 94° C. for 1 min.; 37° C. for 2 min. 72° C. for 2 min. After the last amplification cycle was completed, the samples were heated at 72° C. for 7 min. and then stored overnight at 4° C. Amplification products were isolated and visualized by electrophoresis through an 8% denaturing acrylamide gel (100 W) followed by autoradiography.

A unique band was identified that was present in both the typical and atypical *M. kansasii* strains, but was absent in all non-*M. kansasii* species tested. This band was designated "KATS2." The KATS2 band was excised from the gel, and the DNA was extracted by boiling the acrylamide slice in 100 $\mu$l distilled sterile water for 15 min, followed by ethanol precipitation of the DNA. Five $\mu$l of the extracted DNA was used to re-amplify the KATS2 band by AP-PCR using the primer having the sequence given in SEQ ID NO:1, as described above, with the amplification reaction cycling 35 times as follows: 94° C. for 1 min.; 60° C. for 2 min.; 72° C. for 2 min.

EXAMPLE 2

Cloning of KATS2 *M. kansasii* PCR Product

Fifty ng of the re-amplified KATS2 DNA fragment was cloned into pCRII (Invitrogen; Carlsbad, Calif.), following the protocol provided by the manufacturer. ONE SHOT™ bacterial cells (Invitrogen; Carlsbad, Calif.) were transformed with the pCRII-KATS2 vector. Transformed bacterial colonies were white and were selected by growth on agar containing ampicillin/Xgal (40 mg/ml). Positive colonies were picked and amplified in 25 ml LB media overnight at 37° C. Plasmid DNA was isolated from the bacterial cells using a commercially available plasmid purification kit (Qiagen Plasmid Midi Kit-25, Catalog # 12143; Qiagen, Santa Clarita, Calif.) according to the manufacturer's instructions. The presence of the KATS2 fragment in the isolated plasmid DNA was verified by digesting the plasmid DNA from each positive colony with EcoRI followed by separation by electrophoresis on a 1% agarose gel to confirm that positive colonies contained the appropriate sized DNA insert.

EXAMPLE 3

Southern Blot Hybridization with KATS2 DNA Fragment

The hybridization specificity of the KATS2 DNA fragment to nucleic acids from *M. kansasii* species was evaluated. The KATS2 fragment was hybridized to genomic DNA from various *M. kansasii* and non-*M. kansasii* mycobacteria. 750 ng of genomic DNA from various species of Mycobacteria and non-Mycobacteria was denatured and fixed by dot-blotting onto a ZETA-PROBE™ GT membrane (Bio-Rad). The pCRII vector containing the KATS2 fragment was digested with EcoRI and the small DNA fragment containing KATS2 was purified by electrophoresis and radiolabeled with 32P using the Random Primed DNA Labeling Kit (Boehringer-Mannheim). The 32P-KATS2 DNA fragment was then hybridized to the genomic DNA dot blots from the various Mycobacteria and non-Mycobacteria in 2×hybridization solution (Gibco-BRL) and incubated at 65° C. for 18 hours. Blots were washed in 2× SSC, 0.1% SDS at room temperature and then in 0.1×SSC, 0.1% SDS at 65° C. until background levels of radioactivity were sufficiently reduced. Blots were then rinsed in distilled water and exposed using a Molecular Dynamics Phosphoimager system for 2 hours (Molecular Dynamics World Headquarters, Sunnyvale, Calif.). Exposures were analyzed using ImageQuant V1.1 software provided by Molecular Dynamics (Sunnyvale, Calif.) for use with their Phosphoimager system. The data are summarized below in Table 1. KATS2 hybridized to all 6 of the *M. kansasii* strains tested, both typical and atypical, and out of 17 non-*M. kansasii* Mycobacteria and non-Mycobacteria, only *M. gastri* exhibited a weak cross-reactivity with the KATS2 probe.

TABLE 1

| Organism | Strain | Positive Hybridization |
|---|---|---|
| *M. kansasii* | TMC1201 | Yes |
| *M. kansasii* | LCDC711 | Yes |
| *M. kansasii* | LCDC714 | Yes |
| *M. kansasii* | LCDC715 | Yes |
| *M. kansasii* | LCDC725 | Yes |
| *M. kansasii* | LCDC724 | Yes |
| *M. tuberculosis* | H37Rv | No |
| *M. tuberculosis* | VA44 | No |
| *M. avium* | CDC 33 | No |
| *M. avium* | ATCC 25291 | No |
| *M. intracellulare* | LCDC 1701 | No |
| *M. intracellulare* | ATCC 13950 | No |
| *M. chelonae* | TMC 1543 | No |
| *M. gastri* | LCDC 1301 | Yes - Weak |
| *M. marinium* | LCDC 801 | No |
| *M. smegmatis* | TMC 1533 | No |
| *M. simiae* | CDC 2 | No |
| *A. israeli* | ATCC 10049 | No |
| *C. diphtheria* | ATCC 11813 | No |
| *N. asteroides* | ATCC 3308 | No |
| *R. rhodochrous* | ATCC 13808 | No |
| *S. somaliensis* | ATCC 13201 | No |

EXAMPLE 4

Sequencing of the KATS2 DNA Fragment

The KATS2 fragment cloned into the pCRII vector was sequenced using T7 and SP6 primers (Invitrogen; T7 primer: 5'-TAATACGACTCACTATAGGG-3', SEQ ID NO:2, SP6 primer: 5'-ATTTAGGTGACACTATA-3', SEQ ID NO:3). This sequence information was used to design primers to amplify KATS2 by PCR. An ABI Prism DNA Sequencing Kit (Perkin Elmer) was used to cycle sequence KATS2 in a Perkin Elmer Cetus Model 480 PCR machine. The amplification cycles were run 25 times as follows: 96° C. for 30 sec.; 50° C. for 15 sec.; 60° C. for 4 min. The amplified products were then stored at 4° C. The resulting PCR products were purified according to the protocol provided by Applied Biosystems, Inc. (Foster City, Calif.) and run on an Applied Biosystems 373 DNA Sequencer following the manufacturer's guidelines.

KATS2 was found to have a unique sequence, shown in FIG. 1 (SEQ ID NO:4). The Mycobacteria sequences deposited in the current GENEWORKS™ database were screened with the KATS2 sequence and no matches were identified. A restriction site for the BsoB1 endonuclease is located within the KATS2 sequence. KATS2 specific primers were used to completely resequence the cloned KATS2 fragment from both the 5' and 3' ends of both DNA strands in order to confirm the initial sequencing results. The KATS2 primers were designated E1C (5'-GTTGGCGTGGAGCTGTCT-3'; SEQ ID NO:5), I4 (5'-TCCCTGGCTGCTCTTGAT-3'; SEQ ID NO:6), I5 (5'-ATCAAGAGCAGCCAGGGA-3'; SEQ ID NO:7), I2 (5'-ACAACGTGATGAGGCAGAC-3'; SEQ ID NO:8), and E3 (5'-GGTGGAGATGGAGATGTT-3'; SEQ ID NO:9). The complementary KATS2 target sequence for each primer is indicated in FIG. 1. Primers I5, I2 and E3 are complementary to the opposite strand of the KATS2 DNA fragment from that shown in FIG. 1.

EXAMPLE 5

Cross-Reactivity Studies

The KATS2 PCR primer set E1C/E3 was chosen for PCR amplification using genomic DNA from *M. kansasii*, various species of Mycobacteria, and non-Mycobacteria as template. The PCR reaction was carried out in a total volume of 50 μl Invitrogen PCR Buffer (60 mM Tris-HCl, 15 mM (NH4) 2SO4, pH 8.5) containing 20 ng of DNA template, 0.25 mM each dATP, dTTP, dCTP, dGTP, 1.5 mM Mg+, 0.5 μM primer E1C, 0.5 μM primer E3, 2.5 units Taq polymerase, and Invitrogen Wax Bead. Template DNA was denatured at 95° C. for 2 min. followed by 30 amplification cycles as follows: 94° C. for 1 min., 54° C. for 2 min., 72° C. for 2 min. The amplification products were stored overnight at 4° C.

Amplification by the KATS2 primers was detected by running 10 μl of each PCR amplification reaction mixture on an agarose gel to determine the presence of amplification products. The results are summarized below in Table 2. The KATS2 primers amplified DNA from all 11 *M. kansasii* strains tested, both typical and atypical. Of the 13 non-Mycobacteria species tested, only *M. gastri* showed positive results.

TABLE 2

| Organism | Strain | by PCR |
|---|---|---|
| *M. kansasii* | TMC1201 | Yes |
| *M. kansasii* | LCDC711 | Yes |
| *M. kansasii* | LCDC714 | Yes |
| *M. kansasii* | LCDC725 | Yes |
| *M. kansasii* | T18494 | Yes |
| *M. kansasii* | LCDC724 | Yes |
| *M. kansasii* | T8246 | Yes |
| *M. kansasii* | T1492 | Yes |
| *M. kansasii* | T11792 | Yes |
| *M. kansasii* | T10892 | Yes |
| *M. kansasii* | T8594 | Yes |
| *M. avium* | CDC 33 | No |
| *M. chelonae* | TMC 1543 | No |
| *M. gastri* | LCDC 1301 | Yes - Weak |
| *M. gordonae* | LCDC 1318 | No |
| *M. intracellulare* | LCDC 1701 | No |
| *M. marinium* | LCDC 801 | No |
| *M. simiae* | CDC 2 | No |
| *M. smegmatis* | TMC 1533 | No |
| *M. tuberculosis* | H37Rv | No |
| *C. diphtheria* | ATCC 11913 | No |
| *N. asteroides* | ATCC 3308 | No |
| *R. rhodochrous* | ATCC 13808 | No |
| *S. somaliensis* | ATCC 13201 | No |

EXAMPLE 6

KATS2 Sequence Homology Between PCR Products From *M. kansasii* Strains and *M. gastri*

To determine the degree of similarity in the sequences amplified by the KATS2 primer set, the PCR amplification products obtained in Example 5 were purified using Qiagen's Qiaex II kit according to the manufacturer's instructions. Each purified amplified DNA fragment was used as template for cycle sequencing, as described in Example 4, using multiple primers (E1C, E3, I2, I4 and I5). The KATS2 sequences from typical and atypical *M. kansasii* strains are shown in FIG. 1 (SEQ ID NO:4) and FIG. 2 (SEQ ID NO:10), respectively.

The sequences obtained from the amplified PCR products (SEQ ID NO:4 and SEQ ID NO:10 to SEQ ID NO:17) were aligned as shown in FIG. 3 to deduce a consensus sequence (SEQ ID NO:18) for typical and atypical *M. kansasii* KATS2 sequences. A high level of homology (91.6%) existed between the typical and atypical *M. kansasii* strains, but as anticipated, there was also substantial similarity (86.1%) observed with the *M. gastri* fragment (SEQ ID NO:20) amplified by the KATS2 primers and this region of *M. kansasii* (FIG. 4).

EXAMPLE 7

A KATS2 Subsequence That Hybridizes to *M. kansasii* and Does Not Cross-React With *M. gastri*

The sequence information in FIG. 4 is used to generate *M. kansasii* specific oligonucleotides that distinguish *M. kansasii* from *M. gastri* in DNA amplification and DNA hybridization reactions. The sequences in the region of nucleotides 91 to 100, 120 to 140, and 250 to 275 of the KATS2 region of *M. kansasii* and *M. gastri* show a high degree of sequence divergence. These regions are used to design oligonucleotides that do not cross-hybridize with *M. gastri* under high stringency conditions (e.g., wash stringency of 0.3 M NaCl, 0.03 M sodium citrate, 0.1% SDS at 60° C.). The *M. kansasii* specific oligonucleotides are employed as hybridization probes under conditions as described in Example 3 or as amplification primers under conditions as described in Example 5 to detect *M. kansasii* nucleic acids without substantially hybridizing to, amplifying, or detecting *M. gastri* nucleic acids.

---

That which is claimed is:

1. An isolated oligonucleotide selected from the group consisting of any one of SEQ ID NO:4 through SEQ ID NO:18, at least twenty-five consecutive nucleotides of any one of SEQ ID NO:4 through SEQ ID NO 18, and complements thereof.

2. An oligonucleotide according to claim 1, wherein said oligonucleotide is 25–200 nucleotides long.

3. An oligonucleotide according to claim 2, wherein said oligonucleotide is 25–100 nucleotides long.

4. An oligonucleotide according to claim 3 which is selected from the group consisting of any one of SEQ ID NO:5 through SEQ ID NO:9 and complements thereof.

5. An oligonucleotide according to claim 1 which is linked to a sequence for amplification of a target nucleic acid.

6. An isolated oligonucleotide selected from the group consisting of at least twenty-five consecutive nucleotides of any one of SEQ ID NO:4 through SEQ ID NO:18, and complements thereof, wherein said oligonucleotide does not substantially hybridize to non-*Mycobacterium kansasii* nucleic acids under stringent conditions, defined by a wash stringency of 0.3 M NaCl, 0.03 M sodium citrate, 0.1% SDS at 60° C.

7. An oligonucleotide according to claim 6, wherein said oligonucleotide is 25–200 nucleotides long.

8. An oligonucleotide according to claim 7, wherein said oligonucleotide is 25–100 nucleotides long.

9. An oligonucleotide according to claim 7 which is linked to a sequence for amplification of a target nucleic acid.

10. An isolated oligonucleotide comprising SEQ ID NO:20.

* * * * *

```
SEQUENCE LISTING

(1) GENERAL INFORMATION:

   (iii) NUMBER OF SEQUENCES: 20

(2) INFORMATION FOR SEQ ID NO:1:

     (i) SEQUENCE CHARACTERISTICS:
          (A) LENGTH: 18 base pairs
          (B) TYPE: nucleic acid
          (C) STRANDEDNESS: single
          (D) TOPOLOGY: linear

     (xi) SEQUENCE DESCRIPTION: SEQ ID NO:1:

CGTCATGCTG AAGTCCCT                                               18

(2) INFORMATION FOR SEQ ID NO:2:

     (i) SEQUENCE CHARACTERISTICS:
          (A) LENGTH: 20 base pairs
          (B) TYPE: nucleic acid
          (C) STRANDEDNESS: single
          (D) TOPOLOGY: linear

    (xi) SEQUENCE DESCRIPTION: SEQ ID NO:2:

TAATACGACT CACTATAGGG                                             20

(2) INFORMATION FOR SEQ ID NO:3:

     (i) SEQUENCE CHARACTERISTICS:
          (A) LENGTH: 17 base pairs
          (B) TYPE: nucleic acid
          (C) STRANDEDNESS: single
          (D) TOPOLOGY: linear

    (xi) SEQUENCE DESCRIPTION: SEQ ID NO:3:

ATTTAGGTGA CACTATA                                                17

(2) INFORMATION FOR SEQ ID NO:4:

     (i) SEQUENCE CHARACTERISTICS:
          (A) LENGTH: 309 base pairs
          (B) TYPE: nucleic acid
          (C) STRANDEDNESS: double
          (D) TOPOLOGY: linear

    (ii) MOLECULE TYPE: DNA (genomic)
```

(vi) ORIGINAL SOURCE:
(A) ORGANISM: Mycobacterium kansasii
(B) STRAIN: Strain 1201

(xi) SEQUENCE DESCRIPTION: SEQ ID NO:4:

```
TCAGGTCATG GTCGCCACAG GCGATGCGGC CCAGCCATGC GTCGGCCATC GACGGGTCGG     60

CGTCGGTGGC GGCGACGAAC TCGGGTAACG CGGCCGCTGG TCCCTGGCTG CTCTTGACCG    120

CCATAGCTCG ATCGAAATGC CTACGGGCAG TGAGCAAATC ACCCATCGTA TCCACCATCC    180

TCGACAGCGT GGTGGTATTC GTCCCGAAAG TGGGACGTCC GCCTCATGAC GTTGTGCCGC    240

AACGTTGATC GAGTCACTGT GTAGCAATCG ACATGGTGAC GGGTTCGAGG CTGACGTAAC    300

GGTTCTCGG                                                            309
```

(2) INFORMATION FOR SEQ ID NO:5:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:5:

```
GTTGGCGTGG AGCTGTCT                                                   18
```

(2) INFORMATION FOR SEQ ID NO:6:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:6:

```
TCCCTGGCTG CTCTTGAT                                                   18
```

(2) INFORMATION FOR SEQ ID NO:7:

(i) SEQUENCE CHARACTERISTICS:
(A) LENGTH: 18 base pairs
(B) TYPE: nucleic acid
(C) STRANDEDNESS: single
(D) TOPOLOGY: linear (xi) SEQUENCE DESCRIPTION: SEQ ID NO:7:

```
ATCAAGAGCA GCCAGGGA                                                   18
```

(2) INFORMATION FOR SEQ ID NO:8:

(i) SEQUENCE CHARACTERISTICS:
(A) LENGTH: 19 base pairs
(B) TYPE: nucleic acid
(C) STRANDEDNESS: single
(D) TOPOLOGY: linear (xi) SEQUENCE DESCRIPTION: SEQ ID NO:8:

```
ACAACGTGAT GAGGCAGAC                                                  19
```

(2) INFORMATION FOR SEQ ID NO:9:

(i) SEQUENCE CHARACTERISTICS:
(A) LENGTH: 18 base pairs
(B) TYPE: nucleic acid
(C) STRANDEDNESS: single
(D) TOPOLOGY: linear -continued (ii) MOLECULE TYPE: other nucleic acid (xi) SEQUENCE DESCRIPTION: SEQ ID NO:9:

```
GGTGGAGATG GAGATGTT                                            18
```

(2) INFORMATION FOR SEQ ID NO:10:

(i) SEQUENCE CHARACTERISTICS:
(A) LENGTH: 309 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Mycobacterium kansasii
(B) STRAIN: Strain 1492

(xi) SEQUENCE DESCRIPTION: SEQ ID NO:10:

```
TCAGGTCATG GTCGCCACAG GCGATGCGGC CCAGCCATGC GTCAGCCATC GACGGGTCGG     60

CGTCGGTGGC GGCGACGAAC TCGGGTAACG CGGGTTCTGG TCCCTGGCTG CTCTTGATCG    120

CCATCGCTCG ATCGAAATGC CTACGGGCAG TGAGCAAATC AGCCATTGTA TCCACCATCC    180

TGGACAGCGT GGCGGTAATC GTTCCGCAAC GGGGAAGTCT GCCTCATCAC GTTGTGGCGC    240

AACGTTGATC GAGTCACTTC GTAGCAATCG ACATGGTGAC CGGCTCGAGA CTGACGTAAC    300

GATTTTCGG                                                           309
```

(2) INFORMATION FOR SEQ ID NO:11:

(i) SEQUENCE CHARACTERISTICS:
(A) LENGTH: 309 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Mycobacterium kansasii
(B) STRAIN: Strain 711

(xi) SEQUENCE DESCRIPTION: SEQ ID NO:11:

```
TCAGGTCATG GTCGCCACAG GCGATGCGGC CCAGCCATGC GTCGGCCATC GACGGGTCGG     60

CGTCGGTGGC GGCGACGAAC TCGGGTAACG CGGCCGCTGG TCCCTGGCTG CTCTTGACCG    120

CCATAGCTCG ATCGAAATGC CTACGGGCAG TGAGCAAATC ACCCATCGTA TCCACCATCC    180

TCGACAGCGT GGTGGTATTC GTCCCGAAAG TGGGACGTCC GCCTCATGAC GTTGTGCCGC    240

AACGTTGATC GAGTCACTGT GTAGCAATCG ACATGGTGAC GGGTTCGAGG CTGACGTAAC    300

GGTTCTCGG                                                           309
```

(2) INFORMATION FOR SEQ ID NO:12:

(i) SEQUENCE CHARACTERISTICS:
(A) LENGTH: 309 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Mycobacterium kansasii
(B) STRAIN: Strain 714

(xi) SEQUENCE DESCRIPTION: SEQ ID NO:12:

-continued

```
TCAGGTCATG GTCGCCACAG GCGATGCGGC CCAGCCATGC GTCGGCCATC GACGGGTCGG     60

CGTCGGTGGC GGCGACGAAC TCGGGTAACG CGGCCGCTGG TCCCTGGCTG CTCTTGACCG    120

CCATAGCTCG ATCGAAATGC CTACGGGCAG TGAGCAAATC ACCCATCGTA TCCACCATCC    180

TCGACAGCGT GGTGGTATTC GTCCCGAAAG TGGGACGTCC GCCTCATGAC GTTGTGCCGC    240

AACGTTGATC GAGTCACTGT GTAGCAATCG ACATGGTGAC GGGTTCGAGG CTGACGTAAC    300

GGTTCTCGG                                                            309
```

(2) INFORMATION FOR SEQ ID NO:13:

(i) SEQUENCE CHARACTERISTICS:
(A) LENGTH: 309 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Mycobacterium kansasii
(B) STRAIN: Strain 725

(xi) SEQUENCE DESCRIPTION: SEQ ID NO:13:

```
TCAGGTCATG GTCGCCACAG GCGATGCGGC CCAGCCATGC GTCGGCCATC GACGGGTCGG     60

CGTCGGTGGC GGCGACGAAC TCGGGTAACG CGGCCGCTGG TCCCTGGCTG CTCTTGACCG    120

CCATAGCTCG ATCGAAATGC CTACGGGCAG TGAGCAAATC ACCCATCGTA TCCACCATCC    180

TCGACAGCGT GGTGGTATTC GTCCCGAAAG TGGGACGTCC GCCTCATGAC GTTGTGCCGC    240

AACGTTGATC GAGTCACTGT GTAGCAATCG ACATGGTGAC GGGTTCGAGG CTGACGTAAC    300

GGTTCTCGG                                                            309
```

(2) INFORMATION FOR SEQ ID NO:14:

(i) SEQUENCE CHARACTERISTICS:
(A) LENGTH: 309 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Mycobacterium kansasii
(B) STRAIN: Strain 18494

(xi) SEQUENCE DESCRIPTION: SEQ ID NO:14:

```
TCAGGTCATG GTCGCCACAG GCGATGCGGC CCAGCCATGC GTCGGCCATC GACGGGTCGG     60

CGTCGGTGGC GGCGACGAAC TCGGGTAACG CGGCCGCTGG TCCCTGGCTG CTCTTGACCG    120

CCATAGCTCG ATCGAAATGC CTACGGGCAG TGAGCAAATC ACCCATCGTA TCCACCATCC    180

TCGACAGCGT GGTGGTATTC GTCCCGAAAG TGGGACGTCC GCCTCATGAC GTTGTGCCGC    240

AACGTTGATC GAGTCACTGT GTAGCAATCG ACATGGTGAC GGGTTCGAGG CTGACGTAAC    300

GGTTCTCGG                                                            309
```

(2) INFORMATION FOR SEQ ID NO:15:

(i) SEQUENCE CHARACTERISTICS:
(A) LENGTH: 309 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Mycobacterium kansasii
(B) STRAIN: Strain 724

(xi) SEQUENCE DESCRIPTION: SEQ ID NO:15:

TCAGGTCATG GTCGCCACAG GCGATGCGGC CCAGCCATGC GTCGGCCATC GACGGGTCGG 60

CGTCGGTGGC GGCGACGAAC TCGGGTAACG CGGCCGCTGG TCCCTGGCTG CTCTTGACCG 120

CCATAGCTCG ATCGAAATGC CTACGGGCAG TGAGCAAATC ACCCATCGTA TCCACCATCC 180

TCGACAGCGT GGTGGTATTC GTCCCGAAAG TGGGACGTCC GCCTCATGAC GTTGTGCCGC 240

AACGTTGATC GAGTCACTGT GTAGCAATCG ACATGGTGAC GGGTTCGAGG CTGACGTAAC 300

GGTTCTCGG 309

(2) INFORMATION FOR SEQ ID NO:16:

(i) SEQUENCE CHARACTERISTICS:
(A) LENGTH: 309 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Mycobacterium kansasii
(B) STRAIN: Strain 11792

(xi) SEQUENCE DESCRIPTION: SEQ ID NO:16:

TCAGGTCATG GTCGCCACAG GCGATGCGGC CCAGCCATGC GTCAGCCATC GACGGGTCGG 60

CGTCGGTGGC GGCGACGAAC TCGGGTAACG CGGGTTCTGG TCCCTGGCTG CTCTTGATCG 120

CCATCGCTCG ATCGAAATGC CTACGGGCAG TGAGCAAATC AGCCATTGTA TCCACCATCC 180

TGGACAGCGT GGCGGTAATC GTTCCGCAAC GGGGAAGTCT GCCTCATCAC GTTGTGGCGC 240

AACGTTGATC GAGTCACTTC GTAGCAATCG ACATGGTGAC CGGCTCGAGA CTGACGTAAC 300

GATTTTCGG 309

(2) INFORMATION FOR SEQ ID NO:17:

(i) SEQUENCE CHARACTERISTICS:
(A) LENGTH: 309 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Mycobacterium kansasii
(B) STRAIN: Strain 8246

(xi) SEQUENCE DESCRIPTION: SEQ ID NO:17:

TCAGGTCATG GTCGCCACAG GCGATGCGGC CCAGCCATGC GTCAGCCATC GACGGGTCGG 60

CGTCGGTGGC GGCGACGAAC TCGGGTAACG CGGGTTCTGG TCCCTGGCTG CTCTTGATCG 120

CCATCGCTCG ATCGAAATGC CTACGGGCAG TGAGCAAATC AGCCATTGTA TCCACCATCC 180

TGGACAGCGT GGCGGTAATC GTTCCGCAAC GGGGAAGTCT GCCTCATCAC GTTGTGGCGC 240

AACGTTGATC GAGTCACTTC GTAGCAATCG ACATGGTGAC CGGCTCGAGA CTGACGTAAC 300

GATTTTCGG 309

(2) INFORMATION FOR SEQ ID NO:18:

(i) SEQUENCE CHARACTERISTICS:
(A) LENGTH: 309 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Mycobacterium kansasii (xi) SEQUENCE DESCRIPTION: SEQ ID NO:18:

```
TCAGGTCATG GTCGCCACAG GCGATGCGGC CCAGCCATGC GTCRGCCATC GACGGGTCGG    60

CGTCGGTGGC GGCGACGAAC TCGGGTAACG CGGSYKCTGG TCCCTGGCTG CTCTTGAYCG   120

CCATMGCTCG ATCGAAATGC CTACGGGCAG TGAGCAAATC ASCCATYGTA TCCACCATCC   180

TSGACAGCGT GGYGGTAWTC GTYCCGMAAS KGGGAMGTCY GCCTCATSAC GTTGTGSCGC   240

AACGTTGATC GAGTCACTKY GTAGCAATCG ACATGGTGAC SGGYTCGAGR CTGACGTAAC   300

GRTTYTCGG                                                           309
```

(2) INFORMATION FOR SEQ ID NO:19:

(i) SEQUENCE CHARACTERISTICS:
(A) LENGTH: 311 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Mycobacterium gastri and Mycobacterium kansasii (xi) SEQUENCE DESCRIPTION: SEQ ID NO:19:

```
TCAGGTTCRT GGTTCGCCAC AGGCGATGCG GCCCAGCCAT GCGTCRGCCA TCGACGGGTC    60

GGCGTCGGTG GCGGCGACGA ACTCGGGTAA CGCGKSYKCT GGTCCCWGGC TGCTCYTGAY   120

CGCCATMSCK CGRTCGAAAT GCCTACGGGC AGTGAGCAAA TCASCCATYG TATCCACCAT   180

CCTSGACRGC GTGGYGGTRH TCGTYCCGVM WSKGSGAMGY CYGCCTCATS ACGTTGTGSC   240

GCAACGTTGA TCGAGTCACT KYGYAGCAAT CGACATSGTG ACSGGYTCGA GRCTGACGTA   300

ACGRTTYTCG G                                                        311
```

(2) INFORMATION FOR SEQ ID NO:20:

(i) SEQUENCE CHARACTERISTICS:
(A) LENGTH: 311 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Mycobacterium gastri (xi) SEQUENCE DESCRIPTION: SEQ ID NO:20:

```
TCAGGTTCGT GGTTCGCCAC AGGCGATGCG GCCCAGCCAT GCGTCAGCCA TCGACGGGTC    60

GGCGTCGGTG GCGGCGACGA ACTCGGGTAA CGCGTCCGCT GGTCCCAGGC TGCTCCTGAT   120

CGCCATCCCG CGGTCGAAAT GCCTACGGGC AGTGAGCAAA TCACCCATTG TATCCACCAT   180

CCTCGACGGC GTGGCGGTGC TCGTCCCGGC TGTGCGAAGC CCGCCTCATC ACGTTGTGCC   240

GCAACGTTGA TCGAGTCACT GCGCAGCAAT CGACATCGTG ACCGGCTCGA GGCTGACGTA   300
```

-continued

```
ACGGTTCTCG G                                                          311
```